(12) United States Patent
Reynolds et al.

(10) Patent No.: US 8,383,414 B2
(45) Date of Patent: Feb. 26, 2013

(54) METHODS OF MANUFACTURING A LIGHT GUIDE TEST SENSOR

(75) Inventors: Jeffery S. Reynolds, Granger, IN (US); Steven C. Charlton, Osceola, IN (US); Sung-Kwon Jung, Granger, IN (US); Suny J. George, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 1310 days.

(21) Appl. No.: 11/629,955

(22) PCT Filed: Jul. 1, 2005

(86) PCT No.: PCT/US2005/023771
§ 371 (c)(1),
(2), (4) Date: Dec. 18, 2006

(87) PCT Pub. No.: WO2006/014410
PCT Pub. Date: Feb. 9, 2006

(65) Prior Publication Data
US 2008/0064939 A1 Mar. 13, 2008

Related U.S. Application Data

(60) Provisional application No. 60/585,309, filed on Jul. 2, 2004.

(51) Int. Cl.
*G01N 21/77* (2006.01)
(52) U.S. Cl. ........ 436/169; 436/164; 436/170; 422/400; 422/401; 422/408; 422/420; 422/421; 422/422; 422/423; 422/424; 422/425; 422/426; 422/427; 422/428; 422/429; 422/68.1; 422/82.05; 422/82.06; 422/82.07; 422/82.08; 422/82.09; 422/82.11; 435/13; 435/283.1; 435/287.1; 435/287.7; 435/287.8; 435/287.9; 435/288.7

(58) Field of Classification Search .............. 422/56, 422/82.11, 400, 401, 408, 420, 421, 422, 422/423, 424, 425, 426, 427, 428, 429, 68.1, 422/82.05, 82.06, 82.07, 82.08, 82.09; 436/169, 436/170, 164; 435/13, 283.1, 287.1, 287.7, 435/287.8, 287.9, 288.7
See application file for complete search history.

(56) References Cited

U.S. PATENT DOCUMENTS
(Continued)

FOREIGN PATENT DOCUMENTS

| EP | 0 352 610 A2 | 1/1990 |
|---|---|---|
| EP | 0352 610 A3 | 11/1990 |

(Continued)

OTHER PUBLICATIONS

Written Opinion corresponding to International Patent Application No. PCT/US2005/023771, European Patent Office, dated Nov. 10, 2005, 7 pages.

(Continued)

*Primary Examiner* — Dennis M White
(74) *Attorney, Agent, or Firm* — Nixon Peabody LLP

(57) ABSTRACT

An optic light guide test sensor comprises a light guide, a reagent-coated membrane, and a mesh layer. The reagent-coated membrane and the mesh layer are attached to the light guide at an output end of the light guide. The light guide test sensor is adapted to be used to test the level of an analyte in a biological fluid sample when used with a readhead. A method of manufacturing the light guide test sensor involves providing a plurality of light guides, providing a strip of reagent-coated membrane, and providing a strip of mesh layer. The reagent-coated membrane and mesh layer are attached to the light guides by ultrasonic welding. The reagent-coated membrane and mesh layer may also be attached to the light guides by adhesive.

25 Claims, 5 Drawing Sheets

U.S. PATENT DOCUMENTS

| | | | |
|---|---|---|---|
| 4,764,343 A | 8/1988 | Nyberg | 422/83 |
| 4,849,172 A | 7/1989 | Yafuso et al. | |
| 5,008,077 A | 4/1991 | Kheiri | 422/56 |
| 5,047,627 A * | 9/1991 | Yim et al. | 250/227.23 |
| 5,091,800 A | 2/1992 | Offenbacher et al. | 359/350 |
| 5,098,659 A | 3/1992 | Yim et al. | 422/87.07 |
| 5,110,727 A * | 5/1992 | Oberhardt | 435/13 |
| 5,114,676 A * | 5/1992 | Leiner et al. | 422/82.06 |
| 5,518,689 A | 5/1996 | Dosmann et al. | 422/82.05 |
| 5,525,520 A | 6/1996 | Dinh | |
| 5,611,999 A | 3/1997 | Dosmann et al. | 422/82.05 |
| 5,631,340 A | 5/1997 | Olstein | 528/59 |
| 5,701,181 A | 12/1997 | Boiarski et al. | 356/446 |
| 5,723,284 A | 3/1998 | Ye | 435/4 |
| 5,783,152 A | 7/1998 | Nave | 422/82.06 |
| 6,036,919 A | 3/2000 | Thym et al. | 422/58 |
| 6,137,117 A * | 10/2000 | Feldstein et al. | 250/573 |
| 6,181,417 B1 | 1/2001 | Dosmann | 356/326 |
| 6,190,918 B1 | 2/2001 | Chu et al. | 436/63 |
| 6,207,110 B1 | 3/2001 | Sullivan et al. | 422/56 |
| 6,531,322 B1 | 3/2003 | Jurik et al. | 436/95 |
| 7,262,061 B2 | 8/2007 | Petrich et al. | 436/169 |
| 2002/0169394 A1 | 11/2002 | Eppstein et al. | 600/573 |
| 2003/0077205 A1 | 4/2003 | Xu | 422/82.11 |
| 2003/0157724 A1 | 8/2003 | Petrich et al. | 436/164 |
| 2005/0201897 A1 | 9/2005 | Zimmer et al. | 422/82.05 |
| 2006/0229533 A1 | 10/2006 | Hoenes et al. | 600/584 |

FOREIGN PATENT DOCUMENTS

| | | |
|---|---|---|
| EP | 0 409 033 A2 | 1/1991 |
| EP | 0 448 052 A2 | 9/1991 |
| EP | 0 821 234 B1 | 10/2002 |
| EP | 0 409 033 A2 | 6/2004 |
| EP | 1 424 040 A1 | 6/2004 |
| JP | 4-305143 A | 10/1992 |
| JP | 6-288829 | 10/1994 |
| JP | 9-504873 | 5/1997 |
| JP | 10-111294 | 4/1998 |
| JP | 2001-108621 A | 4/2001 |
| JP | 2002-257706 A | 9/2002 |
| JP | 2004-000599 | 1/2004 |
| RU | 2219525 | 12/2003 |
| RU | 2225006 | 2/2004 |
| WO | WO 01/48461 A1 | 7/2001 |
| WO | WO 2004/107970 A1 | 12/2004 |

OTHER PUBLICATIONS

International Search Report corresponding to International Patent Application No. PCT/US2005/023771, European Patent Office, dated Nov. 10, 2005, 4 pages.

Partial European Search Report corresponding to European Patent Application No. EP 10 18 1942, European Patent Office, dated Mar. 23, 2011, 7 pages.

* cited by examiner

METHODS OF MANUFACTURING A LIGHT GUIDE TEST SENSOR

CROSS-REFERENCE TO RELATED APPLICATION

This application claims priority to application Ser. No. 60/585,309, filed Jul. 2, 2004, which is incorporated by reference in its entirety.

FIELD OF THE INVENTION

The present invention relates generally to testing systems for determining the concentration of an analyte in a fluid sample, and more particularly, to an optical test sensor for use in determining the concentration of an analyte in a biological fluid.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor their blood glucose level.

One method of monitoring a person's blood glucose level is with a portable, hand-held blood glucose testing device. The portable nature of these devices enables users to conveniently test their blood glucose levels at a variety of locations. Some of these devices employ calorimetric testing. In a calorimetric assay, a reagent is designed to produce a colorimetric reaction indicative of a user's blood glucose concentration level. An optical instrument incorporated into the testing device then reads the calorimetric reaction.

A major drawback associated with optical instruments for reading calorimetric reactions is contamination of the optical instrument with biological fluids. Contamination occurs when a biological fluid from a previous sample contacts the optics and is not removed prior to testing the next sample. The presence of a biological fluid from a previous sample can reduce the accuracy of the test result of the current sample by mixing with the current sample or covering a portion of the optics, thus preventing the accurate reading of the current sample. Thus, what is needed is a device that can isolate the optics from the biological fluid sample.

One method of manufacturing current test sensors using traditional manufacturing techniques requires the reagent-coated membrane strip and the mesh layer strip to be cut to the desired size prior to being bonded to a sensor. The small size of the pre-cut reagent-coated membrane and mesh layer makes manufacturing a time consuming, labor intensive, and difficult task. Thus, it would be desirable to have a method of manufacturing a test sensor that is easier to perform.

SUMMARY OF THE INVENTION

According to one embodiment of the present invention an optic light guide sensor comprises a light guide, a reagent-coated membrane, and a mesh layer. The light guide has an input end and an output end. The reagent-coated membrane is at the output end of the light guide. The reagent is adapted to react with a fluid sample to indicate the level of an analyte in the sample. The mesh layer attaches to the membrane.

According to another embodiment, an optic light guide test sensor comprises a light guide, a mesh layer, and a reagent-coated membrane. The light guide has an input end and an output end. The light guide also has protrusions at the output end. A mesh layer attaches to the light guide protrusions. A gap forms between the output end of the light guide and the mesh layer. The gap is adapted to draw in the sample when using the test sensor. A reagent-coated membrane attaches to the mesh layer located at the output end of the light guide. The reagent is adapted to react with a fluid sample to indicate the level of an analyte in the sample.

According to one method of the present invention, the level of an analyte in a biological fluid is tested. The acts of the method provide a light guide test sensor that has a light guide, a reagent-coated membrane, and a mesh layer. A readhead that is adapted to operate in conjunction with the light guide test sensor to test the level of an analyte in a biological fluid is also provided. A person lances an area of the body to produce a fluid sample. A person collects the sample of blood with the reagent-coated membrane and the mesh layer of the light guide test sensor. The person places the light guide test sensor with the collected sample so that the readhead is in position to test the sample. The method measures the light reflected from the sample.

According to another method of the present invention, a light guide test sensor is manufactured. A plurality of light guides having protrusions is provided. A strip of reagent-coated membrane is provided. The method places the strip of reagent-coated membrane onto the plurality of light guides so that the light guide protrusions are in contact with the strip of reagent-coated membrane. Ultrasonic welding melts the protrusions to attach and cut the strip of reagent-coated membrane to the plurality of light guides. The ultrasonic welding attaches and cuts the reagent-coated membrane at about the same time. The light guide is used as a die for the attaching and cutting.

According to a further method of the present invention, a light guide test sensor is manufactured. A plurality of light guides having protrusions is provided. A strip of reagent-coated membrane is provided. A strip of mesh layer is provided. The method places the membrane strip and the mesh strip onto the plurality of light guides so that the light guide protrusions are in contact with the membrane strip, and the mesh strip is in contact with the membrane strip. Ultrasonic welding melts the protrusions to attach and cut the strip of reagent-coated membrane and the strip of mesh layer to the plurality of light guides. The ultrasonic welding attaches and cuts the reagent-coated membrane and the mesh layer at about the same time. The light guide is used as a die for the attaching and cutting.

According to yet another method of the present invention, a light guide test sensor is manufactured. A plurality of light guides are provided that have an adhesive member attached to one end. A strip of reagent-coated membrane is also provided. The membrane strip contacts the plurality of light guides, so that the membrane strip contacts the adhesive members. The membrane strip is cut and attached to the plurality of light guides with a punch as the light guides act as a die. The membrane attaches to the light guide at the adhesive member of the light guide. The membrane is cut and attached to the light guide at about the same time.

According to a further embodiment of the present invention, an optic diffuse light guide sensor comprises an illumination light guide with an input end and an output end. The sensor also has a detection light guide with an input end and an output end, where the detector light guide input end is in close proximity to the illumination light guide output end. A reagent-coated membrane attaches to the output end of the illumination light guide and the input end of the detection light guide. The membrane is illuminated by light from the output end of the illumination light guide. A mesh layer attaches to the reagent-coated membrane and directly contacts the reagent-coated membrane.

According to yet another embodiment of the present invention, an optic reflective-light light guide sensor system comprises a readhead adapted to determine the amount of analyte in a biological sample. The readhead comprises a light source to illuminate the sample as well as illumination optics to guide light through the readhead. The readhead also contains a beam splitter to direct light reflected off the sample to reflectance optics. The reflectance optics direct reflected light to a detector. The detector generates an output signal indicative of the light it receives. The output signal is proportional to the amount of light received. A light guide test sensor collects the a sample to be tested. The light guide test sensor comprises a light guide with an input end and an output end, as well as a reagent-coated membrane and a mesh layer that attach to the output end of the light guide.

Figure 1:
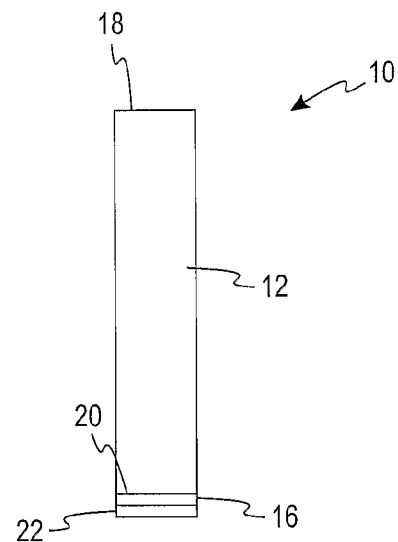
FIG. 1 is a sectional view of the light guide sensor according to one embodiment of the present invention.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DETAILED DESCRIPTION OF THE ILLUSTRATED EMBODIMENT

Referring now to the drawings, and initially to FIG. 1, there is shown a light guide test sensor 10 according to one embodiment of the present invention. In one embodiment, the light guide test sensor 10 is used with a portable handheld glucose testing device for measuring the glucose concentration in the body fluid (e.g., blood, ISF) of a patient. Specifically, the light guide test sensor 10 of the present invention is used in measuring a colorimetric reaction when a reagent reacts with an analyte. The light guide test sensor 10 delivers illuminating light and collects light that reflects off a body fluid sample that reacts on a reagent-coated membrane 16 at one end of a light guide 12. More specifically, the test sensor 10 is used to measure the degree of reagent color change resulting from the reaction. The degree of reagent color change is indicative of the analyte concentration (e.g, glucose, fructoseamine, etc.) in the body fluid. Colorimetric testing is described in detail in U.S. Pat. No. 6,181,417 B1 (entitled "Photometric Readhead with Light Shaping Plate"); U.S. Pat. No. 5,518,689 (entitled "Diffuse Light Reflectance Readhead"); and U.S. Pat. No. 5,611,999 (entitled "Diffuse Light Reflectance Readhead"); each of which is incorporated herein by reference in its entirety.

According to one embodiment of the present invention, the light guide test sensor 10 includes a light guide 12, a reagent-coated membrane 16, and a mesh layer 22. The light guide 12 may be molded with an optically clear material, such as acrylic. In other embodiments, the light guide 12 is molded with other optically clear materials such as, for example, polycarbonate, or polyester.

According to one embodiment, light from a light source is guided through the light guide 12 by total internal reflection. The light directed through the light guide 12 is intended to be read by a readhead. The light guide 12 is able to deliver at its output end 20 a significant amount of the light that is input to the input end 18 of the light guide 12 by the light source. According to one embodiment of the present invention, the light guide 12 has a square cross-section with dimensions of about 2.3 mm by about 2.3 mm and a length of about 5 cm. A square cross section allows mixing of the illuminating and reflecting light so as to minimize the effects of misalignments and manufacturing variations. The light guide 12 delivers light from the light source to the reagent-coated membrane 16 at the output end 20 of light guide 12.

In an alternate embodiment of the present invention, the light guide is a waveguide with a transparent core with a higher reflective index cladding applied. It is further contemplated that the light guide could be a hollow waveguide, or be coated with either absorbing or reflecting layers to enhance the sensor performance.

According to another alternate embodiment of the present invention, the light guide cross section shape may be any polygon with an even number of congruent sides.

In yet another alternate embodiment of the present invention the light guide is tapered, such that the cross sectional area of the light guide at the input end is larger than the cross sectional area of the light guide at its output end.

The reagent-coated membrane 16 is attached to the light guide 12. According to one embodiment, the reagent-coated membrane 16 contains an enzyme, such as glucose oxidase, capable of catalyzing the oxidation reaction of glucose to gluconic acid and hydrogen peroxide and a substance having peroxidative activity capable of catalyzing the oxidation of the indicator. The reagent-coated membrane 16 is a porous polymeric membrane. The membrane 16 may, for example, be made from nylon, nitrocellulose, acrylic polymers, or combinations thereof. The membrane 16 acts as a physical matrix to hold the reagent, and the membrane's pores allow the fluid under analysis to quickly wick into the membrane and react with the reagent. The reagent-coated membrane 16 also serves as a diffuse reflective background so that a reflective measurement may be made. The dye or indicator in the reagent-coated membrane 16 when exposed to blood turns a visually different shade of color, and the shade indicates the glucose level in the blood sample. According to one embodiment of the present invention, a 1 mm diameter light guide requires less than a seventy (70) nanoliter sample size. Reagent-coated membranes are described in further detail in U.S. Pat. No. 6,190,918, which is herein incorporated by reference in its entirety.

In a further alternate embodiment of the present invention, fluorescent or phosphorescent assay may be used in the reagent-coated membrane.

The mesh layer 22 is attached to the reagent-coated membrane 16 and acts to control the volume and distribution of the test sample. As shown in FIG. 1, the mesh layer 22 directly contacts the reagent-coated membrane 16. The mesh layer 22 quickly spreads the fluid sample over the surface of the membrane 16. The fluid sample may move from the mesh layer 22 to the reagent-coated membrane 16. The mesh layer 22 has pore sizes from about 10 microns to about 200 microns. It is further contemplated that mesh layer 22 may contain a wetting agent to further enhance the sample pick-up and further increase the sample distribution over the membrane 16.

Figure 2:
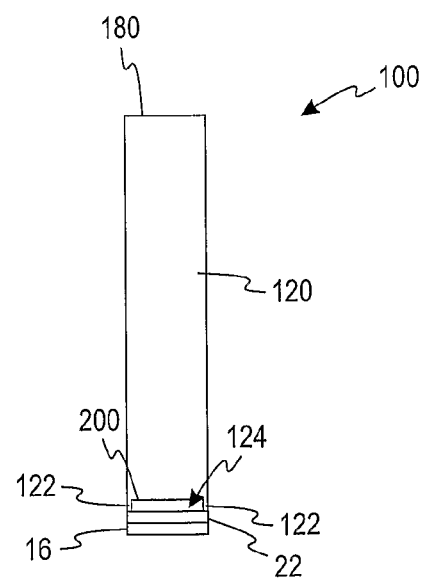
FIG. 2 is a sectional view of the light guide sensor according to another embodiment of the present invention.

According to another embodiment of the present invention depicted in FIG. 2, a light guide test sensor 100 includes a light guide 120, the reagent-coated membrane 16, the mesh layer 22, an input end 180, and an output end 200. The light guide 120 is molded with an optically clear material, such as acrylic. In alternate embodiments, the light guide may be molded with other optically clear materials such as, for example, polycarbonate, or polyester.

Referring still to FIG. 2, the light guide 120 includes protrusions 122. The reagent-coated membrane 16 and the mesh layer 22 are attached to the protrusions 122 of the light guide 120, such that there is a gap 124 between the output end 200 of the light guide 120 and the reagent-coated membrane 16 and mesh layer 22. The gap 124 acts as a capillary channel in this embodiment. The capillary channel formed by gap 124 draws the sample into the gap by capillary action. The use of a capillary channel helps to control the volume of the test sample that the test sensor 100 collects. It is desirable to control the sample volume because it improves the accuracy of the test results.

Figure 3:
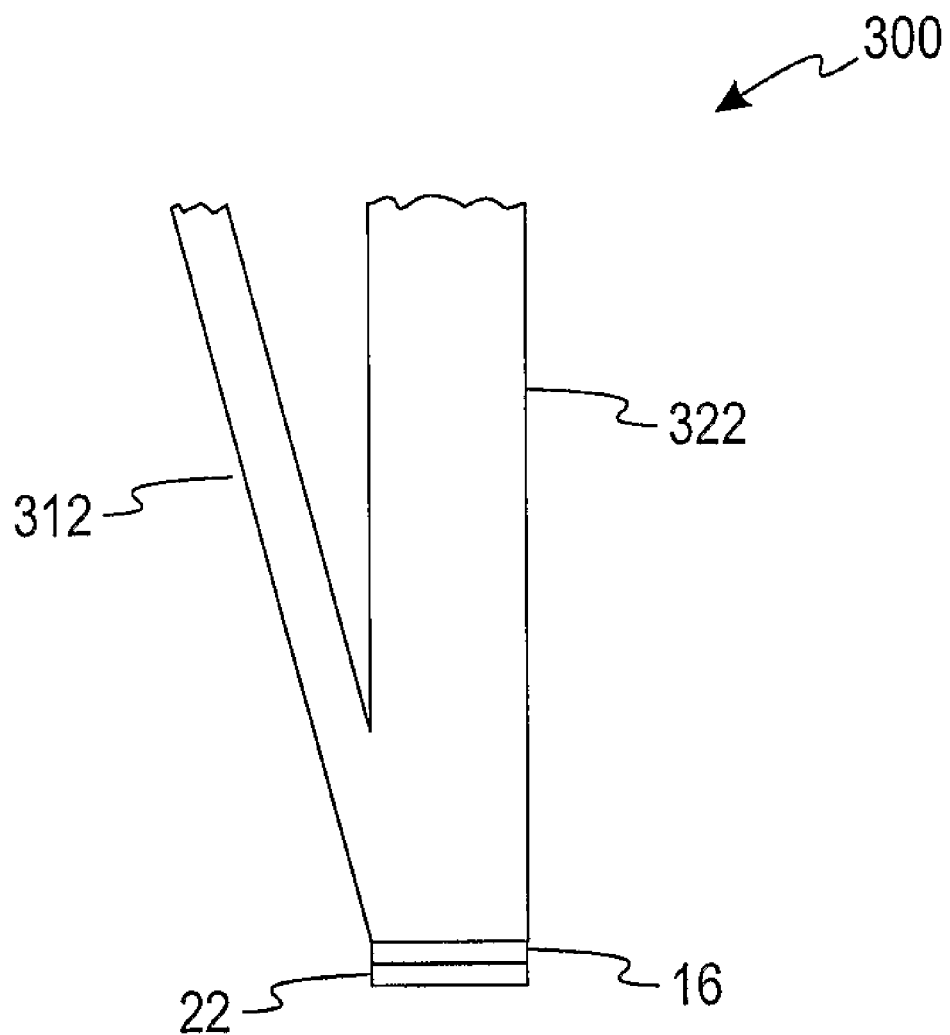
FIG. 3 is a functional block diagram of the test sensor of FIG. 1 with a readhead according to one embodiment of the present invention.

In a further embodiment of the present invention depicted in FIG. 3, a light guide test sensor 300 includes a separate illumination light guide 312 and a detection light guide 322. Light guide sensor 300 further comprises the reagent-coated membrane 16 and the mesh layer 22. According to this embodiment, the light present in detection light guide 322 is that which reflects off of the reagent-coated membrane 16. Having an illumination light guide 312 and a detection light guide 322 lowers the background signal that a readhead detector for reading the light guide is supplied with by reducing the amount of light in the detection light guide 322, thus making the reading more accurate.

Figure 4:
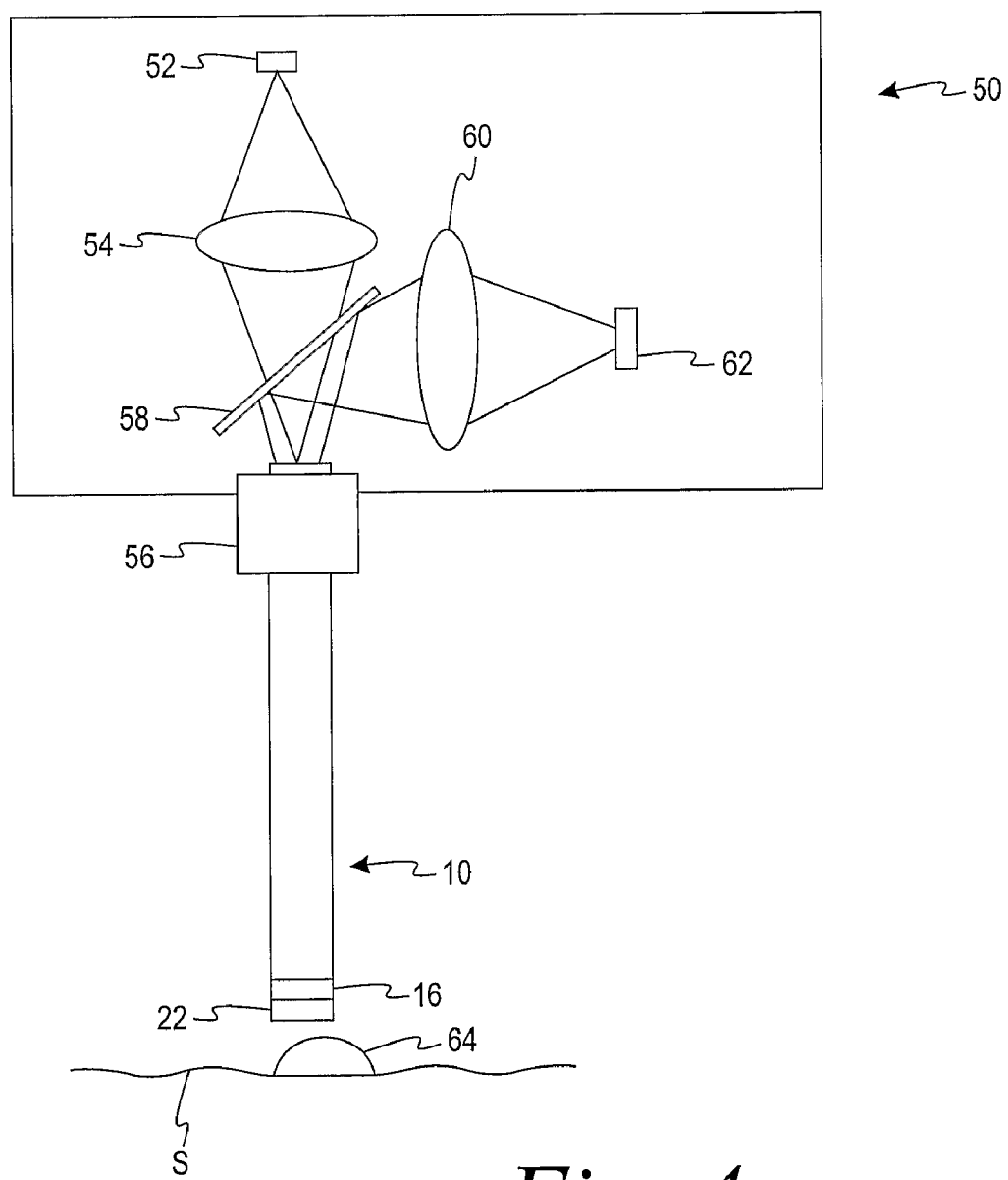
FIG. 4 is a schematic view of a method of manufacturing a light guide sensor according to one embodiment of the present invention.

Referring now to FIG. 4, the light guide test sensor 10 is shown being read by a readhead 50. The readhead 50 contains a light source 52 for producing light, illumination optics 54, a sensor mounting base 56, a beam splitter 58, reflectance optics 60, a detector 62, and electronics (not shown). Meter readheads are described in detail in U.S. Pat. No. 5,611,999 (entitled "Diffused Light Reflectance Readhead"), and U.S. Pat. No. 5,518,689 (entitled "Diffused Light Reflectance Readhead"), each of which is incorporated herein by reference in its entirety.

In one embodiment of the present invention, the light source 52 is a light emitting diode ("LED"). The LED mounts on a printed circuit board, which is part of the electronics that control the operations of the readhead 50. The LED of the light source 52 produces white light. It is further contemplated that a plurality of monochromatic light sources may also be used. Light from the light source 52 passes through the illumination optics 54 of the readhead 50; the illumination optics 54 include an aperture and a lens. A non-limiting example of the illumination optics 54 is a collimation lens that produces a substantially collimated beam of light. The illumination optics 54 directs the light through the beam splitter 58 and a portion of the light is directed into the light guide test sensor 10. Some of the light that arrives at the beam splitter 58 is directed by the beam splitter 58 to a reference detector (not shown). The light that is directed into the light guide sensor 10 reflects off of the test sample that a user applies to the reagent-coated membrane 16.

To obtain a sample for testing, a user lances an area of the user's skin S, such as the user's fingertip, and a drop of blood 64 is produced at the lance site. The user then brings the mesh layer 22 and the reagent-coated membrane 16 end of the light guide test sensor 10 into contact with the blood 64. The blood collects in the reagent-coated membrane 16 and in the mesh layer 22, and the blood reacts with the reagent in the reagent-coated membrane 16 to produce a calorimetric reaction. The user then uses light guide test sensor 10 with the readhead 50 to determine the analyte level present in the sample.

The light that reflects off of the reagent-coated membrane includes light that reflects within the sample. The light guide test sensor 10 collects a portion of the light that reflects within the sample, and directs this light to the readhead 50.

After collecting the reflected light, the light guide test sensor 10 guides the reflected light via the light guide 12 to the readhead 50. The reflected light passes through the beam splitter 58. The beam splitter 58 directs the reflected light from the light guide sensor 10 to the reflectance optics 60, which directs the light onto the detector 62. The detector 62 generates an output signal indicative of the light received by the detector. Devices that can be employed as the detector 62 include charge coupled devices, photocells, and photodiodes. The detector 62 produces an electrical response that is proportional to the reflected light received. The electrical response is interpreted by electronics (not shown). The electronics convert the analog electrical response of the detector 62 into digital data. The electronics also include a microprocessor (not shown) that stores and utilizes digital data to calculate contrast variations indicated by the detector 62 to determine the analyte level present in the sample.

In an alternate embodiment of the present invention, it is further contemplated that the light guide test sensor contains a light trap. A light trap reduces the specular component of light that reflects directly off of the surface of the reagent-coated membrane. Light that reflects off of the surface of the reagent-coated membrane may mix with the light that is reflected off of the sample portion of the reagent-coated membrane causing the reading of the analyte level to be inaccurate. The light trap absorbs this specular component of the light, which increases the accuracy of the test result.

It is also contemplated that the light guide of the light guide test sensor may be optical fibers. According to this alternate embodiment, a plurality of fibers is used as illumination light guides, and a separate plurality of fibers is used as detection light guides. Using a separate plurality of fibers for the detection light guides reduces the background signal that the readhead detector is supplied with, thus making the reading more accurate.

Figure 5:
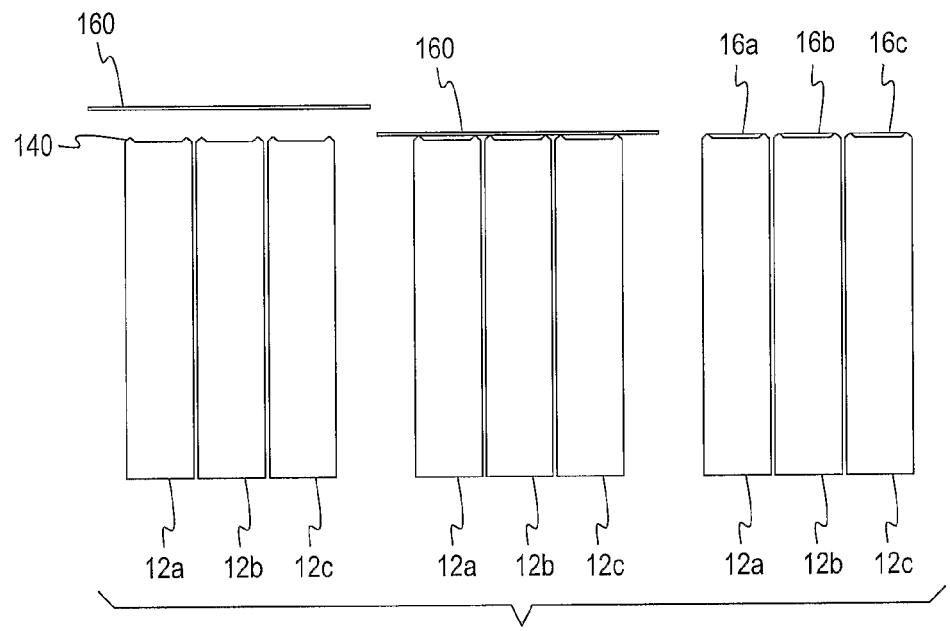
FIG. 5 is a schematic view of a method of manufacturing a light guide sensor according to another embodiment of the present invention.

The light guide test sensor 10 may be manufactured by a method utilizing ultrasonic welding. Ultrasonic welding is a process where high frequency (15 kHz-40 kHz) mechanical vibrations are applied to two or more pieces that are desired to be joined. The vibrations in the material generate heat. This heat causes the materials to melt and form a bond. Pressure may also be exerted on the pieces while the vibrations are applied to ensure a secure bond is formed. According to one embodiment of the present invention, as depicted in FIG. 5, a plurality of light guides 12a-c are provided. The light guides 12a-c include protrusions 140 that act as pointed energy directors, according to one embodiment. The protrusions 140 that act as pointed energy directors are known in the art to act as locations where the ultrasonic energy is concentrated. A strip of reagent-coated membrane 160 is also provided. The strip of reagent-coated membrane 160 is brought in contact with the light guides 12*a-c*. The protrusions 140 contact the reagent-coated membrane strip 160 so that the membrane strip on each respective light guide 12*a-c* is of the desired size, such as the reagent-coated membrane 16 of FIG. 1. The pieces are then subjected to ultrasonic welding. During the ultrasonic welding, the protrusions 140 melt, as they are points of concentration of ultrasonic energy. The melted protrusions 140 cause the reagent-coated membrane to form a bond with respective light guides 12*a-c*. The ultrasonic welding process not only bonds the reagent-coated membrane to the light guide, but it also cuts the reagent-coated membranes 16*a-c* to the desired size, such as reagent-coated membrane 16 of FIG. 1.

Once the reagent-coated membrane 16 is bonded with the light guide, the mesh layer 22 is attached. According to one embodiment, mesh layer 22 is pre-cut to the desired size and adhesively bonded to the reagent-coated membrane 16. Double-sided tape is typically used to form the adhesive bond of the mesh layer 22 to the reagent-coated membrane 16.

In this embodiment, the protrusions 140 are desirable to the manufacturing method as they provide material that will melt to allow the reagent-coated membrane 160 to bond with light guides 12*a-c*. The protrusions 140 are also desirable because they allow the optical properties of light guides 12*a-c* to be minimally affected by the sonic welding process. If the entire output end 20 of the light guide 12 of FIG. 1 were allowed to melt and bond the reagent-coated membrane 16 to the light guide 12, the optical characteristics of the light guide 12 could be adversely affected, and the sensor would not function as accurately.

The use of protrusions 140 allows the light guide 12 to be produced by either a molding or forming process.

Figure 6:
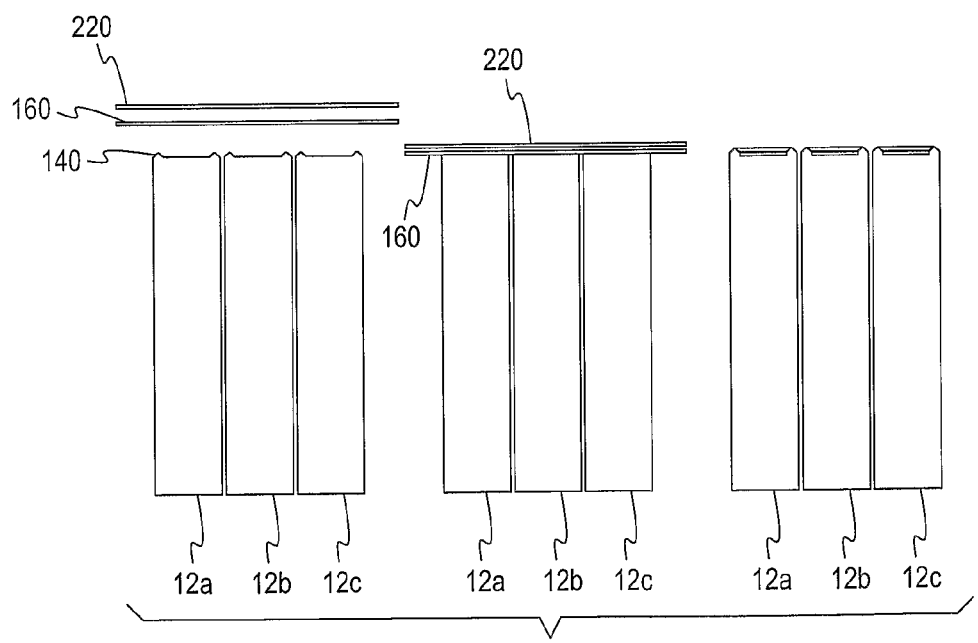
FIG. 6 is a schematic view of a method of manufacturing a light guide sensor according to a further embodiment of the present invention.

Light guide test sensor 10 may be manufactured by a similar method utilizing only ultrasonic welding. Referring to FIG. 6, a plurality of light guides 12*a-c* is provided. The light guides 12*a-c* include protrusions 140 that act as pointed energy directors. A strip of the reagent-coated membrane 160 is provided. A strip of the mesh layer 220 is also provided. The strip of reagent-coated membrane 160 and the strip of mesh 220 are brought in contact with the light guides 12*a-c*. The protrusions 140 contact the reagent-coated membrane strip 160, so that the membrane strip on each respective light guide 12*a-c* is of the desired size, such as reagent-coated membrane 16 of FIG. 1. The portion of mesh strip 220 between the protrusions 140 of light guides 12*a-c* is also the desired size, such as mesh layer 22 of FIG. 1. The pieces are then subjected to ultrasonic welding. During the ultrasonic welding the protrusions 140 that act as pointed energy directors, the reagent-coated membrane strip 160, and the mesh layer strip 220 melt. The melting bonds the reagent-coated membrane and the mesh layer to respective light guides 12*a-c*. This ultrasonic welding manufacturing method is significantly more efficient than traditional methods of manufacturing, as it allows much larger strips of reagent-coated membrane and mesh layer to be cut to the desired size and bonded to the light guides by the ultrasonic welding.

Figure 7:
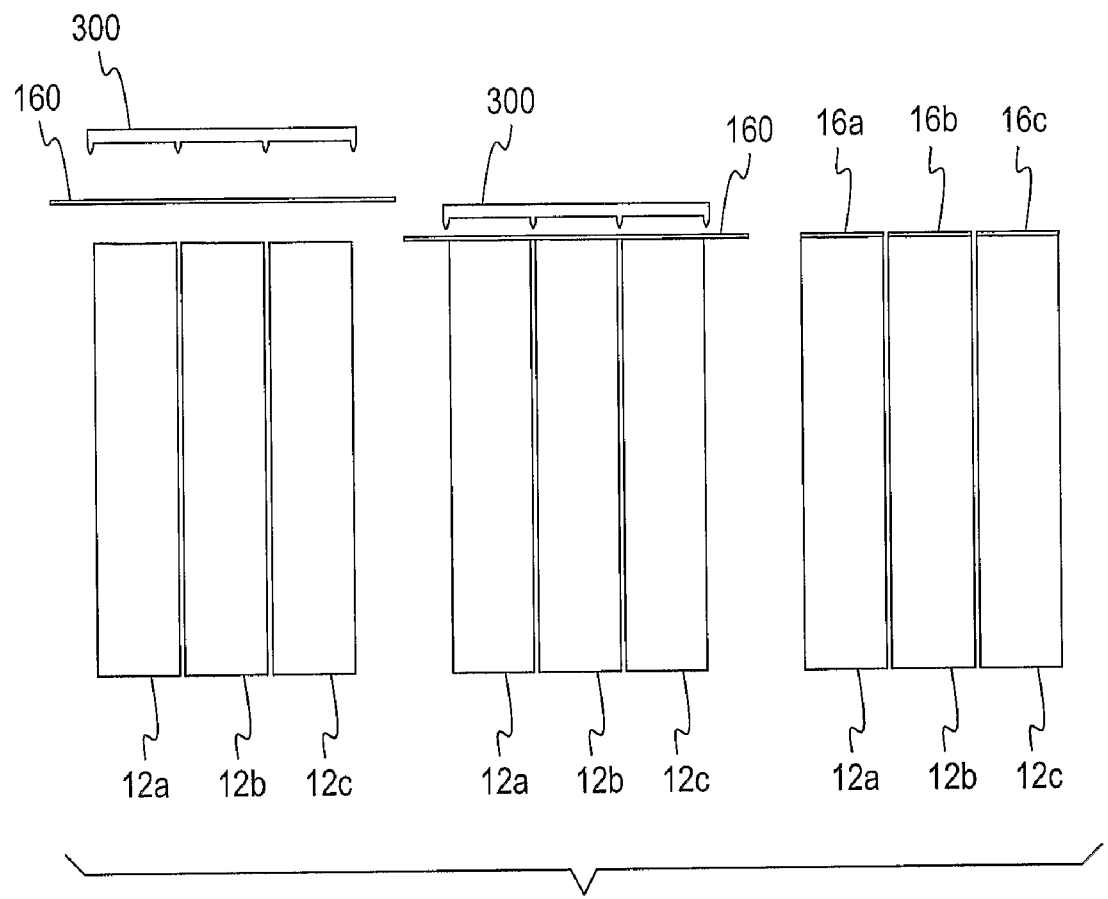
FIG. 7 is a sectional view of the light guide sensor according to a further embodiment of the present invention.

Light guide test sensor 10 may be manufactured by another process using an adhesive to bond the reagent-coated membrane 16 to the light guide 12. According to this embodiment, as depicted in FIG. 7, a plurality of light guides 12*a-c* is provided. A strip of reagent-coated membrane 160 is also provided. An adhesive has been applied to the end of the light guides where the reagent membranes will be attached. An example of an adhesive that might be used in this embodiment is a transparent double sided tape. The strip of reagent-coated membrane 160 contacts light guides 12*a-c*. A punch 300 contacts the strip of reagent-coated membrane 160 and light guides 12*a-c*. The punch uses the light guides 12*a-c* as a die to cut the strip of reagent-coated membrane 160 to the desired size 16*a-c*, such as that of reagent-coated membrane 16 of FIG. 1. The punch also applies pressure to the strip of reagent membrane 160 and light guides 12*a-c* so that once the reagent-coated membrane strip is cut the reagent-coated membrane pieces 16*a-c* that are in contact with light guide 12*a-c* bond to the light guides from the adhesive that had been previously applied to light guides 12*a-c*.

In addition to the embodiments described above, several embodiments of the present invention will now be described.

Alternative Embodiment A

A. An optic light guide test sensor comprising:
a light guide having an input end and an output end;
a reagent-coated membrane, the membrane being located at the output end of the light guide and being attached to the light guide, the reagent being adapted to react with a fluid sample to indicate the level of an analyte in the sample; and
a mesh layer being attached to the membrane.

Alternative Embodiment B

B. An optic light guide test sensor comprising:
a light guide having an input end and an output end, the light guide further comprising protrusions located at the output end;
a mesh layer being attached to the light guide protrusions, the light guide protrusions forming a gap between the output end and the mesh layer, the gap being adapted to draw in the sample when the sensor is being used; and
a reagent-coated membrane, the membrane being attached to the mesh layer located at the output end of the light guide, the reagent being adapted to react with a fluid sample to indicate the level of an analyte in the sample.

Alternative Embodiment C

C. A method of testing the level of an analyte in a biological fluid, the method comprising the acts of:
providing a light guide test sensor, the light guide sensor having a light guide, a reagent-coated membrane, and a mesh layer;
providing a readhead that is adapted to operate in conjunction with the light guide test sensor to test the level of an analyte in the biological fluid;
lancing an area of the body to produce a sample of the biological fluid;
collecting the sample with the reagent-coated membrane and mesh layer of the light guide test sensor;
contacting the light guide test sensor with the collected sample so that the readhead is in position to test the sample; and
measuring the light reflected from the sample.

Alternative Embodiment D

D. The method of alternative embodiment C, wherein the analyte is glucose.

Alternative Embodiment E

E. A method of manufacturing a light guide test sensor, the method comprising the acts of:
providing a plurality of light guides having a first end and a second end, the light guides having protrusions at the first end;
providing a strip of reagent-coated membrane;
placing the membrane strip onto the plurality of light guides so that the light guide protrusions at the first end thereof are in contact with the membrane strip; and
attaching and cutting the membrane strip to the plurality of light guides using ultrasonic welding to melt the protrusions and bond the membrane strip to the plurality of light guides, wherein the attaching and cutting take place at about the same time, and wherein the light guide is used as a die for the attaching and cutting.

Alternative Embodiment F

F. A method of manufacturing a light guide test sensor, the method comprising the acts of:

providing a plurality of light guides having a first end and a second end, the light guides having protrusions at the first end;

providing a strip of reagent-coated membrane;

providing a strip of mesh layer;

placing the membrane strip and the mesh strip onto the plurality of light guides so that the light guide protrusions at the first end thereof are in contact with the membrane strip, and the membrane strip is in direct contact with the mesh strip; and attaching and cutting the membrane strip and the mesh strip to the plurality of light guides using ultrasonic welding to melt the protrusions and bond the membrane strip and the mesh strip to the plurality of light guides, wherein the attaching and cutting take place at about the same time, and wherein the light guide is used as a die for the attaching and cutting.

Alternative Embodiment G

G. A method of manufacturing a light guide test sensor, the method comprising the acts of:

providing a plurality of light guides having an adhesive member attached to one end;

providing a strip of reagent-coated membrane;

contacting the membrane strip to the plurality of light guides so that the light guide adhesive members contact the membrane strip; and attaching and cutting the membrane strip to the plurality of light guides using a punch to cut the membrane strip using the light guides as a die, wherein the membrane is attached to the light guide by the adhesive member, and wherein the cutting and attaching take place at about the same time.

Alternative Embodiment H

H. The method of alternative embodiment G, wherein the adhesive members are double-sided tape.

Alterative Embodiment I

I. A light guide test sensor comprising:

an illumination light guide having an input end and an output end;

a detection light guide having an input end and an output end, the detector light guide input end being in close proximity to the illumination light guide output end;

a reagent-coated membrane, the membrane located at the output end of the illumination light guide and the input end of the detector light guide, the membrane being attached to the illumination light guide and the detector light guide, the membrane being illuminated by a light from the output end of the illumination light guide; and a mesh layer being attached and in direct contact with the membrane.

Alternative Embodiment J

J. The light guide test sensor of alternative embodiment I further comprising a light trap.

Alternative Embodiment K

K. The light guide test sensor of alternative embodiment J, wherein the light trap absorbs a specular component of the light from the output end of the illumination light guide.

Alternative Embodiment L

L. The light guide test sensor of alternative embodiment I, wherein the illumination light guide cross section shape is a polygon with an even number of congruent sides, and the detection light guide cross section shape is a polygon with an even number of congruent sides.

Alternative Embodiment M

M. The light guide test sensor of alternative embodiment L, wherein the illumination light guide cross section shape is square, and the detection light guide cross section shape is square.

Alternative Embodiment N

N. An optic reflective-light light guide sensor system comprising:

a readhead adapted to determine the amount of an analyte in a biological sample, the readhead comprising a light source to provide illumination to a sample to be tested, illumination optics to guide the light produced by the light source through the readhead, a beam splitter adapted to direct light reflected off of the sample to reflectance optics, the reflectance optics being adapted to direct reflected light to a detector, the detector being adapted to generate an output signal indicative of the light received by the detector, the output signal being proportional to the amount reflected light received; and a light guide test sensor adapted to collect a sample, the light guide test sensor comprising a light guide with an input end and an output end, a reagent-coated membrane at the output end of the light guide, and a mesh layer attached to the membrane.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined in the appended claims.

What is claimed is:

1. A method of manufacturing a light guide test sensor, the method comprising the acts of:

providing a plurality of light guides having a respective adhesive member attached to one end, each of the plurality of light guides configured to guide and deliver illuminating light to a fluid sample, and guide and deliver reflected light from the fluid sample, each of the plurality of light guides having structure to contain light being delivered to and from the fluid sample;

providing a strip of reagent-coated membrane, the reagent being adapted to react with a fluid sample to indicate information relating to an analyte in a sample;

contacting the membrane strip to the plurality of light guides by the adhesive member; and attaching and cutting the membrane strip to the plurality of light guides using a punch to cut the membrane strip and using the light guides as a die, wherein the membrane strip is attached to the plurality of light guides by the adhesive member.

2. The method of claim 1, wherein the adhesive member is double-sided tape.

3. The method of claim 1 further included providing a strip of mesh layer and attaching the mesh layer strip to the membrane strip.

4. The method of claim 3 wherein the mesh layer strip is attached to the membrane strip using an adhesive.

5. The method of claim 1 wherein the cutting and attaching take place at about the same time.

6. The method of claim 1 wherein the membrane strip is a porous polymeric membrane.

7. The method of claim 1 wherein the light guide is a waveguide with a transparent core with a reflective index cladding applied thereto.

8. The method of claim 1 wherein the light guide is a hollow waveguide with absorbing layers.

9. The method of claim 1 wherein the light guide is a hollow waveguide with reflecting layers.

10. The method of claim 1 wherein the light guide includes optical fibers.

11. The method of claim 1 wherein the membrane strip includes a fluorescent assay.

12. The method of claim 1 wherein the membrane strip includes a phosphorescent assay.

13. The method of claim 1 wherein the light guide further includes a light trap.

14. A method of manufacturing a light guide test sensor, the method comprising the acts of:
provulating a plurality of light guides having a respective adhesive member attached to one end, each of the light guides being a waveguide or a plurality of optical fibers;
providing a strip of reagent-coated membrane, the reagent being adapted to react with a fluid sample to indicate information relating to an analyte in a sample;
contacting the membrane strip to the plurality of light guides by the adhesive member; and
attaching and cutting the membrane strip to the plurality of light guides using a punch to cut the membrane strip and using the light guides as a die, wherein the membrane strip is attached to the plurality of light guides by the adhesive member.

15. The method of claim 14, wherein the adhesive member is double-sided tape.

16. The method of claim 14 further included providing a strip of mesh layer and attaching the mesh layer strip to the membrane strip.

17. The method of claim 14 wherein the cutting and attaching take place at about the same time.

18. The method of claim 14 wherein the light guide is a waveguide with a transparent core with a reflective index cladding applied thereto.

19. The method of claim 14 wherein the light guide is a hollow waveguide with absorbing layers.

20. The method of claim 14 wherein the light guide is a hollow waveguide with reflecting layers.

21. The method of claim 14 wherein the light guide includes optical fibers.

22. The method of claim 14 wherein the membrane strip includes a fluorescent assay.

23. The method of claim 14 wherein the membrane strip includes a phosphorescent assay.

24. The method of claim 14 wherein the light guide further includes a light trap.

25. A method of manufacturing a light guide test sensor, the method comprising the acts of:
providing a plurality of light guides having a respective adhesive member attached to one end, each of the light guides including a structure in which light is guided by total internal reflection;
providing a strip of reagent-coated membrane, the reagent being adapted to react with a fluid sample to indicate information relating to an analyte in a sample;
contacting the membrane strip to the plurality of light guides by the adhesive member; and
attaching and cutting the membrane strip to the plurality of light guides using a punch to cut the membrane strip and using the light guides as a die, wherein the membrane strip is attached to the plurality of light guides by the adhesive member.

* * * * *

UNITED STATES PATENT AND TRADEMARK OFFICE
CERTIFICATE OF CORRECTION

| | | |
|---|---|---|
| PATENT NO. | : 8,383,414 B2 | Page 1 of 1 |
| APPLICATION NO. | : 11/629955 | |
| DATED | : February 26, 2013 | |
| INVENTOR(S) | : Reynolds et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1435 days.

Signed and Sealed this
Eighteenth Day of November, 2014

Michelle K. Lee
*Deputy Director of the United States Patent and Trademark Office*